US008150117B2

(12) United States Patent
Breeuwer et al.

(10) Patent No.: US 8,150,117 B2
(45) Date of Patent: Apr. 3, 2012

(54) METHOD AND APPARATUS FOR DETERMINING STRESS IN AN ANATOMICAL STRUCTURE

(75) Inventors: Marcel Breeuwer, Eindhoven (NL); Sander De Putter, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 821 days.

(21) Appl. No.: 12/293,105

(22) PCT Filed: Mar. 9, 2007

(86) PCT No.: PCT/IB2007/050791
§ 371 (c)(1),
(2), (4) Date: Sep. 16, 2008

(87) PCT Pub. No.: WO2007/107904
PCT Pub. Date: Sep. 27, 2007

(65) Prior Publication Data
US 2009/0129645 A1 May 21, 2009

(30) Foreign Application Priority Data
Mar. 17, 2006 (EP) .................................... 06111323

(51) Int. Cl.
*G06K 9/00* (2006.01)

(52) U.S. Cl. ........................................ 382/128; 382/134
(58) Field of Classification Search .................. None
See application file for complete search history.

(56) References Cited

U.S. PATENT DOCUMENTS
7,805,177 B2 * 9/2010 Chen et al. .................... 600/407

OTHER PUBLICATIONS

Speelman L et al: "Effects of Wall Calcifications in Patient-Specific Wall Stress Analyses of Abdominal Aortic Aneurysms" Transactions of the ASME. Journal of Biomechanical Engineering ASME USA, vol. 129, No. 1, Feb. 2007, pp. 105-109, XP008089145 ISSN: 0148-0731.
Inzoli F et al: "Biomechanical Factors in Abdominal Aortic Aneurysm Rupture." European Journal of Vascular Surgery Nov. 1993, vol. 7, No. 6, Nov. 1993, pp. 667-674, XP008089411 ISSN: 0950-821X.
Wang David H J et al: "Effect of Intraluminal Thrombus on Wall Stress in Patient-Specific Models of Abdominal Aortic Aneurysm." Journal of Vascular Surgery : Official Publication, The Society for Vascular Surgery [and] International Society for Cardiovascular Surgery, North American Chapter Sep. 2002, vol. 36, No. 3, Sep. 2002, pp. 598-604, XP002472217 ISSN: 0741-5214.
Vorp David A et al: "Biomechanical Determinants of Abdominal Aortic Aneurysm Rupture."Arteriosclerosis, Thrombosis, and Vascular Biology Aug. 2005, vol. 25, No. 8, Aug. 2005 pp. 1558-1566, XP002472216 ISSN: 1524-4636.

(Continued)

*Primary Examiner* — Minh N Tang

(57) ABSTRACT

A method of determining wall stress in an abdominal aortic aneurysm is disclosed. The method includes determining, from anatomical image data, respective first stress values at locations on the wall, based on the aorta having substantially uniform stiffness. The primary direction of stress those locations are determined, and the locations of calcified regions (20) are then determined. The distance to the nearest calcified region is then determined for each location not corresponding to a calcified region, and the additional stress caused by the calcified regions is then determined from values stored in a memory.

18 Claims, 3 Drawing Sheets

OTHER PUBLICATIONS

Raghavan M L: "Automated Methodology for Determination of Stress Distribution in Human Abdominal Aortic Aneurysm" Journal of Biomechanical Engineering, American Society of Mechanical Engineers, US, vol. 127, No. 5, Oct. 20, pp. 868-871, XP008089146 ISSN: 0148-0731.

S. D. Williamson, et al: On the Sensitivity of Wall Stresses in Diseased Arteries to Variable Material Properties, Journal of Biomechanical Engineering, 2003 by ASME, Feb. 2003, vol. 125, pp. 147-155.

Jun Inagaki, et al: Construction of Reference Data for Classification of Elasticity Images of Arterial Wall, 2004 IEEE Ultrasonics Symposium, 2004 IEEE International Ultrasonics, Ferroelectrics, and Frequency Control Joint 50th Anniversary Conference, pp. 2161-2164.

Raghavan M L et al: Wall Stress Distribution on Three-Dimensionally Reconstructed Models of Human Abdominal Aortic Aneurysm, Journal of Vascular Surgery, vol. 31. No. 4, Apr. 2000, pp. 760-769, XP-002472224.

* cited by examiner

METHOD AND APPARATUS FOR DETERMINING STRESS IN AN ANATOMICAL STRUCTURE

The present invention relates to method and apparatus for determining stress in an anatomical structure, and relates particularly, but not exclusively, to a method and apparatus for determining stress in a wall of the abdominal aorta in which calcified regions are present.

Medical diagnosis of vascular diseases and therapeutic decisions are primarily based on the anatomy and morphology of diseased blood vessels, information about which is derived from medical images. For example, the diagnosis of abdominal aortic aneurysm (AAA), which is dilatation of the abdominal aorta and usually leads directly to death when it ruptures, and the decision to perform surgical repair, is based on the diameter of the AAA. This is usually measured on the basis of ultrasound and/or Computed Tomography Angiography (CTA) images. Intervention is usually performed if the diameter is more than 55 mm.

However, a small but significant percentage of AAA's rupture before their diameter reaches 55 mm, and a significant percentage of patients that cannot be operated on (for example as a result of cardiac condition) develop a non rupturing AAA with a diameter significantly more than 55 mm (up to 80 mm). It can therefore be seen that the diameter is an inaccurate indicator of rupture risk.

It has been found that the peak wall stress in the AAA is a better indicator of rupture risk than the diameter of the AAA. It is known to derive the geometry of the AAA outer wall from CTA images and then assume a wall of constant thickness with constant material properties for the complete AAA. The peak wall stress is then calculated and the position of this peak wall stress on the AAA is determined.

This known method suffers from the disadvantage that it does not use patient-specific wall material properties and wall thickness, which limits the accuracy of the results achieved. Attempts have also been made to incorporate the effect of calcifications in the vessel wall, but this approach does not accurately represent the geometry of the calcifications. Also, since calcifications generally have complex shapes and may be small in relation to the AAA Structures, accurate geometric modeling of these calcifications leads to computationally complex numerical models.

Preferred embodiments of the present invention seek to overcome the above disadvantages of the prior art.

According to an aspect of the present invention, there is provided a method of determining stress in an anatomical structure, the method comprising:

determining, from anatomical image data, respective first stress values at a plurality of locations in said structure, based on said structure having stiffness within a first range;

determining a plurality of first said locations at which the stiffness of said anatomical structure is within a second range, different from said first range; and determining, at a plurality of second said locations different from said first locations, respective second stress values, representing respective said first stress values corrected to take into account said anatomical structure having stiffness in said second range at at least one said first location.

By calculating first stress values on the basis of the structure having stiffness in a first range, and then calculating second stress values corrected to take into account regions of stiffness in a second range different from the first range, this enables patient-specific first stress values, and more general second stress values to be calculated. For example, in the case of AAAs, this enables patient-specific first stress values based on the first stiffness range to be calculated, and then second stress values based on more general corrections to take regions of calcification into account. This provides the advantage of enabling the stress in the aorta wall to be calculated as accurately, but significantly more quickly, than in known methods.

The method may use finite-element modeling.

The method may be a method of determining wall stress in a blood vessel.

The second locations may correspond to areas of calcification in said blood vessel.

Said locations may be selected by means of a volume mesh.

Said second stress values may be determined by means of values stored in a memory.

According to another aspect of the present invention, there is provided an apparatus for determining stress in an anatomical structure, the apparatus comprising at least one processor for:

determining, from anatomical image data, respective first stress values at a plurality of locations in said structure, based on said structure having stiffness within a first range;

determining a plurality of first said locations at which the stiffness of said anatomical structure is within a second range, different from said first range; and determining, at a plurality of second said locations different from said first locations, respective second stress values, representing respective said first stress values corrected to take into account said anatomical structure having stiffness in said second range at at least one said first location.

At least one said processor may be adapted to use finite-element modeling.

The apparatus may be adapted to determine wall stress in a blood vessel.

The second locations may correspond to areas of calcification in said blood vessel.

Said locations may be determined by means of a volume mesh.

Said second stress values may be determined by means of values stored in a memory.

According to a further aspect of the present invention, there is provided a data structure for use by a computer system for determining stress in an anatomical structure, the data structure comprising:

first computer code executable to determine, from anatomical image data, respective first stress values at a plurality of locations in said structure, based on said structure having stiffness within a first range;

second computer code executable to determine a plurality of first said locations at which the stiffness of said anatomical structure is within a second range, different from said first range; and third computer code executable to determine, at a plurality of second said locations different from said first locations, respective second stress values, representing respective said first stress values corrected to take into account said anatomical structure having stiffness in said second range at at least one said first location.

The data structure may be executable to use finite-element modeling.

The data structure may be executable to determine wall stress in a blood vessel.

The second locations may correspond to areas of calcification in said blood vessel.

Said locations may be determined by means of a volume mesh.

The third computer code may be executable to determine said second stress values by means of values stored in a memory.

A preferred embodiment of the invention will now be described, by way of example only and not in any limitative sense, with reference to the accompanying drawings, in which.

Figure 5:
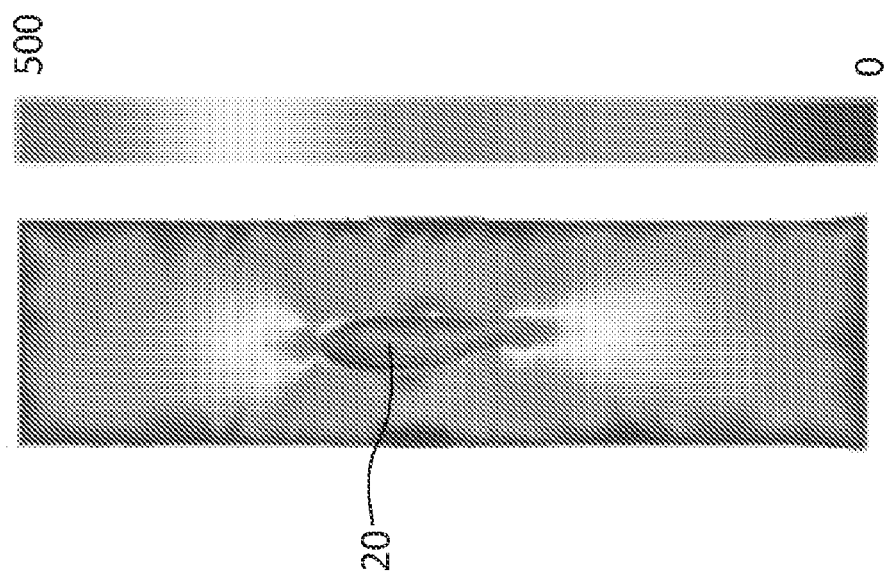
Figure 4:
Figure 4:
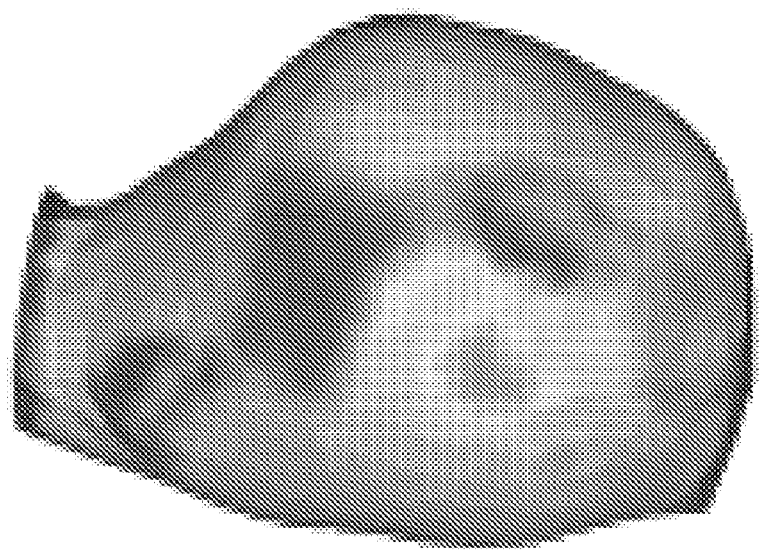

FIG. 4 indicates an illustration of peak wall stress for an AAA without taking calcifications into account; and FIG. 5 is an illustration of the wall stress induced in the wall of an AAA by a calcification, determined by means of a method embodying the present invention.

Figure 1:
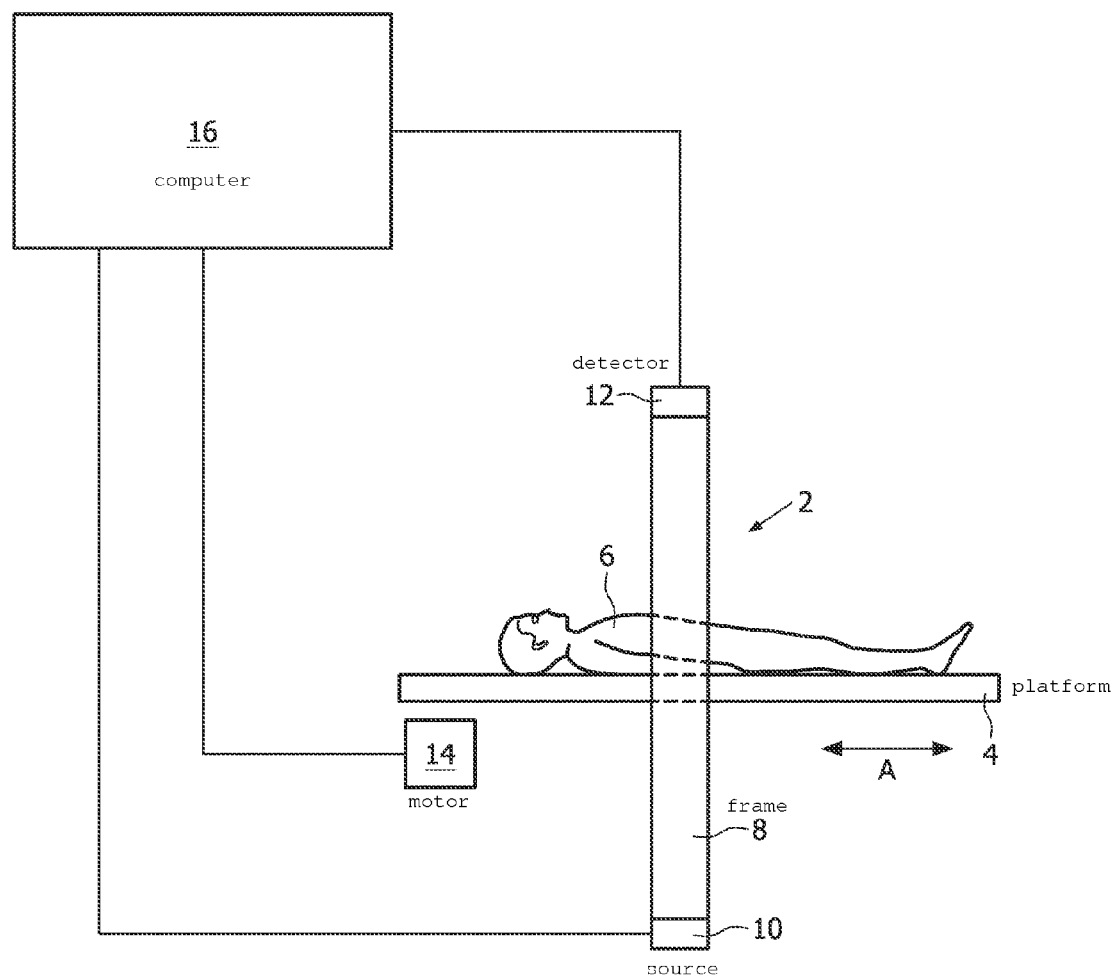
FIG. 1 is a schematic representation of a medical imaging apparatus embodying the present invention.

Referring to FIG. 1, a medical imaging apparatus 2 embodying the present invention is disclosed. The apparatus 2 includes a platform 4 for supporting a patient 6 within a circular frame 8 having opposed pairs of x-ray sources 10 and detectors 12 for imaging a patient's heart. The platform 4 supporting patient 6 is transported in the direction of arrow A by means of a motor 14, the sources 10, detectors 12 and motor 14 being controlled by a computer 16, which also reconstructs a three dimensional model of the patient's heart from image data obtained by the sources 10 and detectors 12. This aspect of the operation of the apparatus 2 will be well known to persons skilled in the art and will therefore not be described in further detail.

Figure 2:
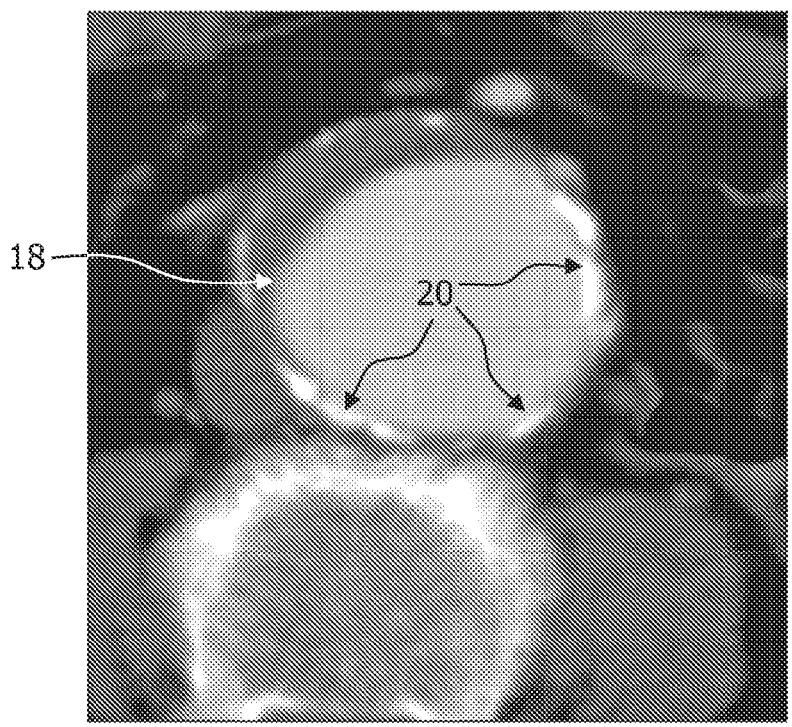
FIG. 2 is a slice of a 3D Computed Tomography Angiography (CTA) image acquisition of an Abdominal Aortic Aneurysm (AAA) indicating the presence of calcified regions.
Figure 3:
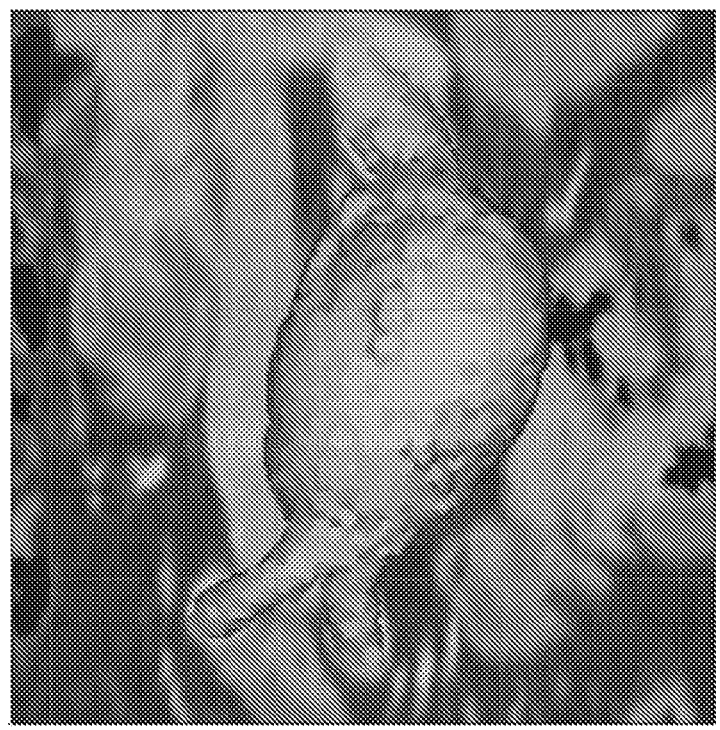
FIG. 3 illustrates automatically segmented AAA outer wall geometry of the AAA of FIG. 2.

Referring to FIG. 2, a slice of a 3D CTA image of an AAA 18 having calcified regions 20 is shown. In order to determine the peak wall stress in the AAA 18, the AAA outer wall geometry is first automatically segmented by the computer 16, to provide the image shown in FIG. 3, by means of one of more methods which will be familiar to persons skilled in the art. First stress values are then determined by assuming uniform stiffness of the AAA shown in FIG. 3, and the wall stress is calculated for a number of locations arranged on a volume mesh, by means of finite-element modeling. This then provides the graphic representation of the peak wall stress as indicated in FIG. 4.

In order to take account of the effect of the calcified regions 20 on the wall stress, the primary direction of stress is determined at each of the positions for which the wall stress has been determined. As will be appreciated by persons skilled in the art, in determining wall stress by means of finite element modeling, the primary direction of stress is the direction of the largest eigenvector of the tensor representing stress.

The locations of calcified areas are then determined, and the distance, in the primary stress direction, to the closest region of calcification is measured for each location not corresponding to a calcified region. This enables the additional stress induced by various types of calcification to be determined on the basis of pre-calculated values stored in a table, and as illustrated in FIG. 5. This general use table is used to calculate second stress values to take account of calcifications in the arrangement shown in FIGS. 3 and 4.

The process of the present invention has the advantage that a patient-specific finite-element based calculation of the stress in vessel walls with calcified areas can be performed in a few hours on a standard computer, as a result of which the results achieved are as accurate as those of existing methods, but can be obtained much more rapidly.

It will be appreciated by persons skilled in the art that the above embodiment has been described by way of example only and not in any limitative sense, and that various alterations and modifications are possible without departure from the scope of the invention as defined by the appended claims.

The invention claimed is:

1. A method of determining stress in an anatomical structure, the method executed by a processor and comprising:
   determining, from anatomical image data, respective first stress values at a plurality of locations in said structure, based on said structure having stiffness within a first range;
   determining a plurality of first said locations at which the stiffness of said anatomical structure is within a second range, different from said first range; and
   determining, at a plurality of second said locations different from said first locations, respective second stress values, representing respective said first stress values corrected to take into account said anatomical structure having stiffness in said second range found in at least one said first location.

2. A method according to claim 1, wherein the method uses finite-element modeling.

3. A method according to claim 1, wherein the method is a method of determining wall stress in a blood vessel.

4. A method according to claim 3, wherein the second locations correspond to areas of calcification in said blood vessel.

5. A method according to claim 1, wherein said locations are determined by means of a volume mesh.

6. A method according to claim 1, wherein said second stress values are determined by means of values stored in a memory.

7. An apparatus for determining stress in an anatomical structure, the apparatus comprising at least one processor for:
   determining, from anatomical image data, respective first stress values at a plurality of locations in said structure, based on said structure having stiffness within a first range;
   determining a plurality of first said locations at which the stiffness of said anatomical structure is within a second range, different from said first range; and
   determining, at a plurality of second said locations different from said first locations, respective second stress values, representing respective said first stress values corrected to take into account said anatomical structure having stiffness in said second range found in at least one said first location.

8. An apparatus according to claim 7, wherein at least one said processor is adapted to use finite-element modeling.

9. An apparatus according to claim 7, wherein the apparatus is adapted to determine wall stress in a blood vessel.

10. An apparatus according to claim 9, wherein the second locations correspond to areas of calcification in said blood vessel.

11. An apparatus according to claim 7, wherein said locations are determined by means of a volume mesh.

12. An apparatus according to claim 7, wherein said second stress values are determined by means of values stored in a memory.

13. A data structure for use by a computer system for determining stress in an anatomical structure, the data structure comprising:
   first computer code executable by a processor to determine, from anatomical image data, respective first stress values at a plurality of locations in said structure, based on said structure having stiffness within a first range;

second computer code executable by a processor to determine a plurality of first said locations at which the stiffness of said anatomical structure is within a second range, different from said first range; and third computer code executable by a processor to determine, at a plurality of second said locations different from said first locations, respective second stress values, representing respective said first stress values corrected to take into account said anatomical structure having stiffness in said second range found in at least one said first location.

14. A data structure according to claim 13, wherein the data structure is executable to use finite-element modeling.

15. A data structure according to claim 13, wherein the data structure is executable to determine wall stress in a blood vessel.

16. A data structure according to claim 15, wherein the second locations correspond to areas of calcification in said blood vessel.

17. A data structure according to claim 13, wherein said locations are determined by means of a volume mesh.

18. A data structure according to claim 13, wherein the third computer code is executable to determine said second stress values by means of values stored in a memory.

* * * * *